United States Patent [19]

Massirio et al.

[11] Patent Number: 5,248,838
[45] Date of Patent: Sep. 28, 1993

[54] PROCESS FOR PREPARING BISPHENOL FLUORENE COMPOUNDS

[75] Inventors: Sergio Massirio, Finale Ligure; Mauro Besio, Vado Ligure; Marcello Gagliano, Finale Ligure; Brunella Fornasari, Genoa; Angelo Vallarino, Spotorno; Piera Di Mito, Savona, all of Italy

[73] Assignee: Minnesota Mining and Manufacturing Company, St. Paul, Minn.

[21] Appl. No.: 773,628

[22] PCT Filed: Oct. 16, 1991

[86] PCT No.: PCT/US91/07666
§ 371 Date: Jan. 24, 1992
§ 102(e) Date: Jan. 24, 1992

[87] PCT Pub. No.: WO92/07812
PCT Pub. Date: May 14, 1992

[30] Foreign Application Priority Data

Oct. 30, 1990 [IT] Italy ............... 21918 A/90

[51] Int. Cl.$^5$ ............ C07C 37/20; C07C 39/00
[52] U.S. Cl. .................... 568/727; 568/718
[58] Field of Search ........... 568/727, 722, 717, 718, 568/719, 720

[56] References Cited

U.S. PATENT DOCUMENTS

| | | |
|---|---|---|
| 2,359,242 | 9/1944 | Perkins et al. |
| 3,546,165 | 12/1970 | Winthrop ............ 568/719 |
| 3,821,317 | 6/1974 | Webb et al. ............ 568/719 |
| 3,944,583 | 3/1976 | Quinn ............ 568/719 |
| 3,947,468 | 3/1976 | Hall et al. ............ 568/719 |
| 3,968,083 | 7/1976 | Quinn ............ 568/170 |
| 4,024,194 | 5/1977 | Corn, Jr. |
| 4,049,721 | 9/1977 | Corn, Jr. et al. ............ 568/719 |
| 4,387,209 | 6/1983 | Rieder et al. ............ 568/719 |
| 4,388,454 | 6/1983 | Rieder et al. |
| 4,430,493 | 2/1984 | Rieder |
| 4,446,195 | 5/1984 | Rieder et al. |
| 4,467,122 | 8/1984 | Szabolcs ............ 568/719 |
| 4,503,266 | 3/1985 | Szabolcs ............ 568/719 |
| 4,675,458 | 6/1987 | Riemann et al. |

FOREIGN PATENT DOCUMENTS

| | | |
|---|---|---|
| 489747 | 6/1976 | Australia . |
| 0065060 | 11/1982 | European Pat. Off. . |
| 0180133 | 5/1986 | European Pat. Off. ........ 568/719 |
| 0314007 | 5/1989 | European Pat. Off. ........ 568/719 |
| 2948222 | 7/1981 | Fed. Rep. of Germany . |
| 63-152622 | 6/1988 | Japan ............ 568/720 |
| 1122201 | 7/1968 | United Kingdom ........ 568/718 |
| 1322173 | 7/1973 | United Kingdom . |
| 1449207 | 9/1976 | United Kingdom . |

OTHER PUBLICATIONS

Aromatic Polyesters with Large Cross-Planar Substituents, P. W. Morgan, Macromolecules, vol. 3, pp. 536-544 (1970).

Chemical Abstract: CA 86:5963b bis(hydroxyphenyl)alkanes—Australian Pat. 474,155.

Chemical Abstract: CA 97:198587r Synthesis of bisphenol A—Nippon Kagaku Kaishi 1982, 1363-70.

Primary Examiner—Werren B. Lone
Attorney, Agent, or Firm—Gary L. Griswold; Walter N. Kirn; Eloise J. Maki

[57] ABSTRACT

A process for preparing bisphenol fluorene products which comprises reacting fluorenone with a phenol compound in the presence of an acidic condensing agent in a solution of an organic liquid wherein the bisphenol fluorene compound is insoluble and recovering the obtained bisphenol fluorene product from the reaction mixture.

19 Claims, No Drawings

PROCESS FOR PREPARING BISPHENOL FLUORENE COMPOUNDS

FIELD OF THE INVENTION

The present invention relates to a process for preparing bisphenol fluorene products, in particular 9,9-bis-(4-hydroxyphenyl)-fluorene. More in particular, the invention relates to reacting fluorenone with a phenol compound and an acidic condensing agent in the presence of an organic solvent to produce the aforementioned products.

BACKGROUND OF THE ART

Bisphenol fluorene products, and in particular 9,9-bis-(4-hydroxyphenyl)-fluorene (hereinafter, for brevity referred to as BPF) having the formula

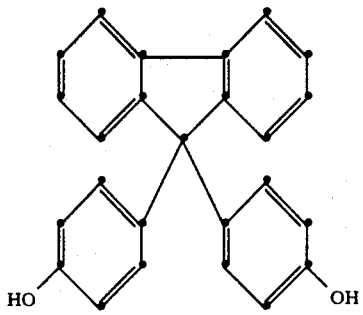

are extensively used as monomers in the manufacture of polycondensation products. For example, BPF can be reacted with phosgene to make polycarbonate resins, or else it can be reacted with organic acid dihalides such as terephthaloyl chloride, isophthaloyl chloride, etc., to make polyester resins. Polycondensation products and processes are described, for example, by P. W. Morgan in Macromolecules. Vol. 3, page 536 (1970), and in U.S. Pat. Nos. 3,944,583, 3,968,083, 3,546,165, in GB Pat. No. 1,122,201, in JP Pat. Publ. Nos. 192432/82 and 152622/88 Polycondensation products obtained from bisphenol fluorene products, in particular from BPF, have been found to have good flammability resistance and oxygen indices making them useful, for example, as insulation for electrical conductors, motor slot liners, films and high temperature coatings.

A number of processes have been described in the art for the preparation of bisphenol fluorene products. Generally, such process comprise the condensation of fluorenone with a phenol compound in the presence of acidic condensing agents. BPF can be prepared, as disclosed by P. W. Morgan in *Macromolecules*, Vol. 3, page 536 (1970), by reacting fluorenone with phenol in the presence of betamercapto propionic acid and anhydrous hydrogen chloride. U.S. Pat. No. 4,467,122 describes a process for the preparation of BPF by reacting fluorenone and phenol in the presence of anhydrous hydrogen chloride, and, as an additional condensation agent, at least one soluble bivalent, trivalent or tetravalent metal halide of a metal selected from the group consisting of Ca, Fe, Ti, Zn, Sn and Al. U.S. Pat No. 4,675,458 describes a process for preparing BPF wherein fluorenone and phenol are reacted in the presence of sulfuric acid (having a concentration greater than 70 percent) and beta-mercapto propionic acid.

In the processes described above, the phenol is generally employed in excess of its stoichiometric amount in order to keep the reaction mixture stirrable. For example, the use of as much as six moles of phenol per mole of fluorenone (U.S. Pat. No. 4,675,458) has been reported as useful. If excess phenol is employed in the reaction, it may be present in the BPF product as an impurity and in the waste materials remaining after recover and purification of crude BPF product from the reaction mixture.

Various methods of recovering the crude BPF product from the reaction mixture and purifying it have been described. For example, the reaction mixture may be diluted with water and boiled until a solid material comprising the crude BPF compound forms. This solid material can then be recovered from the reaction mixture and further purified. Alternatively, the reaction mixture may be steam distilled to remove excess phenol and other volatile impurities prior to recovery of the crude BPF product. In either of these methods, the crude BPF product may be washed with water, dissolved in an organic solvent and crystallized from the organic solvent to further reduce impurities such as unreacted phenol. U.S. Pat. No. 4,503,266 describes a process in which the reaction mixture is combined with hot isopropanol and the resulting mixture is then added to a ten-fold volume of water to precipitate the crude BPF. Alternatively, U.S. Pat. No. 4,503,266 describes a process employing molten phenol in which the reaction mixture is in the form of a crude crystalline paste at the end of the reaction. The paste is then diluted with hot water to form additional precipitate, and the diluted mixture is centrifuged and washed with boiling water to remove impurities such as excess phenol. U.S. Pat. No. 4 049 721 describes a process of extracting impurities such as residual phenol from crude BPF product by mixing the crude BPF product with methanol in an amount sufficient to solubilize all of the impurities, filtering the mixture to remove solid material, adding water to the filtrate which contains BPF as a suspension, heating the resulting mixture and then cooling the mixture to crystallize out purified BPF.

The disadvantage of these recovery and purification processes is that they generate large volumes of aqueous waste containing a low concentration of phenol. These aqueous wastes are environmentally hazardous and the phenol either must be recovered from aqueous waste before disposal or the aqueous wastes must be incinerated. Thus, these processes may result in high waste disposal costs so it would be advantageous to make BPF product using a process which does not generate large volumes of aqueous waste contaminated with a low concentration of phenol compounds.

SUMMARY OF THE INVENTION

The present invention provides a novel process for preparing crude bisphenol fluorene product by condensation reaction of fluorenone with a phenol compound in the presence of at least one acidic condensing agent, the process comprising the steps of:

A) preparing a mixture comprising fluorenone and phenol compound dissolved or dispersed in a body of organic liquid, the bisphenol fluorene compound being insoluble in the organic liquid at ambient temperature;

B) reacting the mixture prepared in step A) in the presence of at least one acidic condensing agent at a temperature effective to promote a reaction between the fluorenone and phenol compound, and maintaining the temperature for a sufficient time to achieve the desired level of reaction completion between the fluorenone and phenol compound, optionally adding additional organic liquid to the reaction mixture during the reaction to improve stirrability of the reaction mixture;

C) cooling the resulting mixture to a temperature effective to promote the precipitation of a crude bisphenol fluorene product; and D) recovering the crude bisphenol fluorene product, the product having less than 20 weight percent of the phenol compound, from the reaction mixture.

Since the recovered bisphenol fluorene product is in its crude form, it may, if desired, be further purified using any of the methods known in the art. For example, it may be washed with water and, if necessary, dissolved in an organic solvent and crystallized from the resulting solution. These purification steps may be performed one or more times as necessary.

Preferably, the acidic condensing agent is selected from the group consisting of organic sulfonic acid condensing agents and mixtures thereof and the phenol compound is used substantially in its stoichiometric amount, and more preferably in less than 20 percent excess of its stoichiometric amount, most preferbly in less than 10 percent excess of its stoichiometric amount.

In another aspect, the present invention provides crude bisphenol fluorene product having less than 20 weight percent, preferably less that 5 weight percent, and more preferably less than 1 weight percent, of the phenol compound after recovery from a reaction mixture initially comprising fluorenone and the phenol compound.

The process of the present invention permits preparation of crude bisphenol fluorene product without causing the pollution problems associated with the processes of the prior art. The process also results in a crude product which contains less than 20 weight percent, preferably less than 5 weight percent, and more preferably less than 1 weight percent of the phenol compound. Thus, less purification of this crude product must be performed to achieve a purified bisphenol fluorene product having the desired amount of the phenol compound.

In contrast to many of the processes of the prior art, the reaction mixture may be maintained in a readily stirrable condition throughout the reaction permitting more effective cooling of the reaction mixture and promoting more complete reaction of the reactants. More effective cooling of the reaction mixture may lead to the formation of fewer isomers of the desired bisphenol fluorene compound, fewer dimers of fluorenone and less unreacted fluorenone in the crude bisphenol fluorene product. The isomers, dimers and unreacted fluorenone are impurities in the bisphenol fluorene product which must be removed before using the product in many applications. Generally, such impurities are removed by washing the bisphenol fluorene product or crystallizing the bisphenol fluorene product from an organic solvent (e.g., 1,2-dichloroethane) using any of the processes known in the art. Thus, crude bisphenol fluorene product prepared using the process of this invention may require less purification after recovery from the reaction mixture to achieve a highly pure product (e.g., 99.8 and preferably 99.95% pure or as measured by HPLC).

Additionally the process of the present invention when using organic sulfonic acid condensing agents overcomes the disadvantages of processes associated with hydrochloric acid and sulfuric acid as condensing agents. Hydrochloric acid is highly corrosive to metal equipment and sulfuric acid may form sulfonated products.

Examples of bisphenol fluorene compounds which may be prepared using the process of this invention include 9,9-bis-(4-hydroxyphenyl)-fluorene (BPF), 9,9-bis-(3-methyl-4-hydroxyphenyl)-fluorene, 9,9-bis-(3-ethyl-4-hydroxyphenyl)-fluorene, 9,9-bis-(3,5-dichloro-4-hydroxyphenyl)-fluorene, and 9,9-bis-3,5-dibromo4-hydroxyphenyl)-fluorene.

DETAILED DESCRIPTION OF THE INVENTION

The organic liquids useful in this invention are those which are good solvents or dispersants for the fluorenone and phenol compounds over a wide range of temperatures. That is, the organic liquid should maintain the fluorenone and phenol compounds in solution or dispersion at temperatures at least as high as the temperature at which the fluorenone and phenol compounds are reacted, and at least as low as the temperature to which the reaction mixture is cooled to facilitate precipitation or crystallization of the bisphenol fluorene product. The organic liquid also should not react with the fluorenone, phenol compound, acidic condensing agents or bisphenol fluorene compound. Representative organic liquids which are useful in this invention include non-polar hydrocarbon solvents such as benzene, toluene, xylene, cyclohexane, hexane, heptane, nitromethane, halogenated hydrocarbons (e.g., trichloroethylene, 1,2-dichloroethane, methylene chloride and sym-tetrachloroethane) and mixtures thereof. For reasons of economy, toxicology, and availability, toluene is particularly useful as the organic liquid.

Typically the organic liquid is the major component by volume of the reaction mixture. Optionally, an additional effective amount of the organic liquid may be added to the reaction mixture during the reaction to maintain the reaction mixture in a readily stirrable condition. Typically, the amount of the organic liquid initially used to prepare the reaction mixture is about 10 and preferably 50 volume percent or more of the volume of the organic liquid present in the reaction mixture at the end of the reaction. Typically, this amount will constitute about 5% to 30% weight percent of the initial reaction mixture. It is important not to add too much additional organic liquid to the reaction mixture during the reaction because too much liquid will prevent the precipitation of the bisphenol fluorene product from the reaction mixture. Thus, the bisphenol fluorene product should be equal to 0.7 to 1.5 times the weight of the organic liquid at the end of the reaction.

Phenol compounds useful in this invention are those which will react with fluorenone via a condensation reaction. Typically, these compounds include substituted and unsubstituted phenol compounds. Representative phenol compounds include phenol, 3-ethyl-phenol, 3,5-dichlorophenol, 3,5-dibromo-phenol, 2-methyl-phenol, 2-ethylphenol, 2,6-dimethyl-phenol and 2-chloro-phenol. Preferably, the phenol compound is anhydrous and is employed in the reaction in an amount in excess of its stoichiometric amount. It is believed that a stoichiometric excess of the phenol compound may promote a higher reaction rate, so some excess may be desirable, however, large excesses are not required as may be required in prior art processes to maintain stirrability of the reaction mixture. Thus, while amounts of the phenol compound up to three times its stoichiometric amount are useful in this invention (i.e., six moles of phenol compound per mole of fluorenone), amounts only 1.5 times the stoichiometric amount are also useful.

In particular, when in the present invention an organic sulfonic acid is used as acidic condensing agent, the phenol compound may be employed in the reaction in substantially stoichiometric amount. It has been found that a substantially stoichiometric amount of the phenol compound, combined with the organic sulfonic acid condensing agent and the organic solvent, may allow a complete reaction in few hours (4 to 12) at low reaction temperatures (30° C. to 60° C.), without requiring the large excesses of phenol compound used in prior art processes (i.e., six moles of phenol compound per mole of fluorenone). Thus, the excess of phenol of less than 0.2 times the stoichiometric amount, and preferably less than 0.1 times the stoichiometric amount can be useful in this invention.

The acidic condensing agents useful in this invention are known in the art. For example hydrogen chloride, sulfuric acid, divalent, trivalent or tetravalent halides (as described in U.S. Pat. No. 4,467,122), mercaptans and mercapto carboxylic acid (as described in U.S. Pat. No. 4,675,458) are useful in this invention. Optionally, more than one acidic condensation agent may be employed in the reaction. Any of the known means of combining the acidic condensing agent and the reaction mixture so that the phenol compound and the fluorenone may react in the presence of the condensing agent are useful in this invention. For example, gaseous hydrogen chloride may be bubbled through the reaction mixture over the course of the reaction. Alternatively, the acidic condensing agent or agents may be added to the reaction mixture at the beginning of the reaction. When more than one condensing agent is used, one condensing agent may be added to the reaction mixture at the beginning of the reaction and the other may be added slowly over the course of the reaction. In order to promote good mixing and a complete reaction, the reaction mixture must be continuously stirred once the acidic condensing agents are added. Preferably, the acidic condensing agent is either a mixture of concentrated sulfuric acid, preferably used in an amount from 0.3 to 2 moles per mole of fluorenone, and beta-mercapto propionic acid, preferably used in an amount from 0.0004 to 0.2 moles per mole of fluorenone, or a mixture of gaseous hydrogen chloride bubbled through the reaction mixture and aluminum trichloride, preferably employed in an amount from 0.1 to 0.3 moles per mole of fluorenone.

Most preferably, the acidic condensing agent useful in this invention is selected from the group consisting of organic sulfonic acids. Organic sulfonic acids are organic compounds containing one or more sulfo groups linked to an organic radical. For example, methanesulfonic acid, ethanesulfonic acid, benzenesulfonic acid, p-toluenesulfonic acid, 2,4-toluene-disulfonic acid, 1-piperidinesulfonic acid, 2-butadienesulfonic acid and the like are useful in this invention. Preferably, the acid condensing agent is methanesulfonic acid. Optionally, more than one organic sulfonic acid condensing agent may be employed in the reaction. In particular and preferably in this invention, the organic sulfonic acid condensing agents are used in combination with a small amount of an organic thiol compound as co-catalyst. Examples of organic thiol compounds include ethyl mercaptan, n-butyl mercaptan, 1-octyl mercaptan, t-dodecyl mercaptan, mercaptoethanol, mercaptoacetic acid and beta-mercapto propionic acid, and the use of these compounds in the preparation of 9,9-bis-(4-hydroxyphenyl)-fluorene is described in U.S. Pat. No. 4,675,458. Preferably, beta-mercapto propionic acid is used as co-catalyst. Preferably, the acidic condensing agent is a mixture of methanesulfonic acid, preferably used in an amount from 0.3 to 2 moles per mole of fluorenone, and beta-mercapto propionic acid, preferably used in an amount from 0.0004 to 0.2 moles per mole of fluorenone.

The process of this invention may be effected in a batch or a continuous type operation. For example, when a batch-type operation is used, the fluorenone, phenol compound and a quantity of the organic liquid are placed in an appropriate apparatus such as a jacketed reaction kettle equipped with a stirring mechanism and agitated. If the acidic condensing agents are to be added at the beginning of the reaction, they may be added to kettle with the other ingredients, or they may be added to an agitated mixture of the fluorenone, phenol compound and organic liquid. If the acidic condensing agent is to be added during the course of the reaction, it may be added slowly to the agitated mixture, for example by bubbling. Once the acidic condensing agent has been added or has begun to be added to the reaction mixture, the mixture is heated to the desired reaction temperature and maintained thereat for the duration of the reaction. Preferably, the reaction temperature is below 80° C., more preferably between 20° and 70' C. and most preferably between 40° and 60° C. Since the reaction mixture can be maintained is a readily stirrable condition throughout the reaction, it can also be more efficiently cooled. This is important because if the reaction mixture cannot be cooled the temperature of the reaction mixture may increase. One effect of a temperature increase (e.g. to a temperature greater than 65° C.) may be that more isomers, dimers and other impurities may form in the reaction mixture. At the end of the reaction, the reaction mixture is cooled to a temperature sufficiently low to effect precipitation or crystallization of the bisphenol fluorene product. Temperatures as low as ambient temperature (i.e., 25° C.) may be effective to cause precipitation, but preferably lower temperatures (e.g., 0° C.) are used. The precipitated bisphenol fluorene product is then recovered from the remaining reaction mixture by filtration or centrifugation and, if desired, subjected to washing and crystallization from an organic solvent before drying. The remaining reaction mixture will retain most of the unreacted phenol. Typically, at least 80% and preferably at least 99% by weight of the unreacted phenol will be retained in the organic liquid. The volume of the remaining reaction mixture is smaller than the volume of phenol-contaminated aqueous waste produced by prior art processes and it is much easier to incinerate. Thus it is believed the waste materials produced by the process of this invention are much easier to handle and dispose of that those produced by the processes of the prior art.

It is also contemplated within the scope of the process of this invention that the preparation of bisphenol fluorene products by the solution condensation of fluorenone with a phenol compound may also be effected in a continuous manner, although not necessarily with equivalent results. For example, when a continuous type operation is used, the starting materials dissolved in an organic liquid are fed continuously to a reaction zone which is maintained at proper operating conditions of temperature and stirring. After a desired residence time, the reaction effluent is continously discharged to isolate the desired bisphenol fluorene product.

The following examples are given to illustrate the process of the present invention, but are not intended to limit the scope of the present invention in any manner whatsoever.

EXAMPLE 1

In a 3 l four necked flask, 360 g (2 moles) of fluorenone were dissolved in 565 g (6 moles) of melted phenol and 850 ml of anhydrous toluene. 62.4 g of $AlCl_3$ were charged and gaseous HCl was bubbled through the dispersion under stirring, maintaining the temperature between 57° and 60° C. These conditions were maintained for 30 hours to obtain a complete reaction of fluorenone. The crystalline dispersion was cooled at 0° C., filtered, the solid washed on the filter with a little amount of cooled toluene, then with water and dried into an air circulating oven at 80° C. to obtain 562 g of a BPF having the following composition: BPF 96.41%, phenol traces, fluorenone 0.63%, isomer 2.0% and dimer 0.94%. The filtration of the reaction mass gave about 1550 ml of toluene solution having the following composition: phenol 15.5%, BPF 5.9%, fluorenone 1.0%, isomer 1.0% and dimer 1.9%. The result given by this analysis is that more than 90 of the phenol excess has been removed from the product in the filtration mother liquors. Two crystallizations from organic solvent gave a higher than 99.8% pure BPF.

EXAMPLE 2

The same reactant quantities and the same operational conditions of Example 1 were used, with the exception that trichloroethylene was used instead of toluene. 515 g of crude product was obtained having the following composition: BPF 97.0%, phenol 0.4%, fluorenone 0.11%, isomer 1.9% and dimer 0.6%. Two crystallizations form organic solvent gave a higher than 99.8% pure BPF.

EXAMPLE 3

The same reactant quantities and the same operational conditions of Example 1 were used, with the exception that sym-tetrachloroethane was used instead of toluene. 502 g of crude product were obtained having the following composition: BPF 95.0%, phenol 1.7%, fluorenone 0.05%, isomer 2.2% and dimer 1.0%. Two crystallization from organic solvent gave a higher than 99.8% pure BPF.

EXAMPLE 4

In a 1 l four necked flask were charged 90 g of fluorenone, 188 g of phenol, 120 ml of toluene, 0.4 ml of beta-mercapto propionic acid. The temperature of the reaction mixture was maintained at 30° C. In 30 minutes 15 ml of 96% $H_2SO_4$ were added dropwise; the temperature raised to 50° C. and then was set at 55°-60° C. After 40 minutes from the first addition of $H_2SO_4$, crystallization of BPF started without stopping the stirring. After 2 hours the reaction mixture was heated to reflux for half an hour and the mixture was then cooled to room temperature. The solid BPF was filtered, washed on the filter with toluene, then with water. After drying in an air ventilated oven at 80° C., 150 g or crude BPF were obtained. After two crystallizations from organic solvent a higher than 99.8% pure BPF was obtained.

EXAMPLE 5

In a 500 ml four necked flask equipped with stirrer, reflux condenser and thermometer, 45 g (0.25 moles) of fluorenone were charged together with 49.4 g (0.525 moles) of melted phenol. 120 ml of toluene were added and the mixture was stirred to dissolve reactants. Then 0.2 ml (2.3 mmoles) of 3-mercapto-propionic acid and 18 ml (0.28 moles) of methanesulfonic acid were charged to the flask. The temperature increased to 42° C. in 30 minutes, then external heating was provided in order to reach and maintain 55° C. After one hour, the crystallization of BPF occurred and the reaction was complete after six hours. After cooling at room temperature for one hour, the reaction mixture was filtered and washed with 50 ml of toluene, then with 4×100 ml of water. After drying, 70.4 g of crude BPF were obtained, having the following composition: BPF 96.71%, fluorenone approximately zero, isomer 1.75%, dimer 0.91%, phenol 0.61%. Two crystallizations from organic solvent gave a higher than 99.8% pure BPF.

EXAMPLE 6

In a 500 ml four neck flask equipped with stirrer, reflux condenser and thermometer, 45 g (0.25 moles) of fluorenone were charged together with 49.4 g (0.525 moles) of melted phenol. 120 ml of methylene chloride were added and the mixture was stirred to dissolve reactants. Then 0.2 ml (2.3 mmoles) of 3-mercapto-propionic acid and 18 ml (0.28 moles) of methanesulionic acid were charged to the flask. The temperature increased up to 48° C. in 30 minutes, and then external heating was provided to maintain the refluxing temperature. After two hours, the crystallization of BPF occurred and the reaction was complete after ten hours. After cooling at room temperature for one hour, the reaction mixture was filtered and washed with 30 ml of methylene chloride, then with 4×100 ml of water. After drying, 66.4 g of crude BPF were obtained, having the following composition: BPF 99.16%, fluorenone approximately zero, isomer 0.11%, dimer 0.51%, phenol 0.11%. Two crystallizations from organic solvent gave a higher than 99.8% pure BPF.

EXAMPLE 7

In a 500 ml four necked flask equipped with stirrer, reflux condenser and thermometer, 45 g (0.25 moles) of fluorenone were charged together with 47.4 g (0.5 moles) of melted phenol. 120 ml of methylene chloride were added and the mixture was stirred to dissolve reactants.. Then 0.2 ml (2.3 mmoles) of 3-mercapto-propionic acid and 18 ml (0.28 moles) of methanesulfonic acid were charged to the flask. The temperature increased up to 48° C. in 30 minutes, and then external heating was provided to maintain the refluxing temperature. After two hours, the crystallization of BPF occurred and the reaction was complete after ten hours. After cooling at room temperature for one hour, the reaction mixture was filtered and washed with 30 ml of methylene chloride, then with 4×100 ml of water. After drying, 63 g of crude BPF were obtained, having the following composition: BPF 97.06%, fluorenone approximately zero, isomer 0.26%, dimer 1.96%, phenol 0.19%. Two crystallizations from organic solvent gave a higher than 99.8% pure BPF.

COMPARATIVE EXAMPLE C1

90 g (0.5 mole) of fluorenone and 188 g (2 moles) of phenol were heated to 30° C. in a 500 ml four necked flask equipped with a stirrer, dropping funnel and reflux condenser. 0.4 ml (4.6 mmoles) of beta-mercapto propionic acid were added. The mixture was cooled with iced water and 20 ml (0.36 mole) of 96% $H_2SO_4$ were added in such a way that the temperature could be held in the range from 30° to 70° C. (addition time was of 5 minutes). A complete crystallization of the reaction mass occurred after the addition of $H_2SO_4$. After additional 20 minutes at 50°-60° C., 220 ml of methanol were added and the mixture heated until a complete solution was obtained. The solution was poured into a 3 l becker and, under stirring, 2 l of water were added. After stirring for one hour, the solid BPF was separated by filtration, washed with water and dried. A purity of 99.85%, determined with HPLC (High Pressure Liquid Chromatography), was obtained after two crystallizations using two organic solvents. Yield 60%.

We claim:

1. A process for preparing crude bisphenol fluorene product by condensation reaction of fluorenone with a phenol compound in the presence of at least one acidic condensing agent, the process comprising the steps of:
   A) preparing a mixture comprising fluorenone and phenol compound dissolved or dispersed in a body of organic liquid, the bisphenol fluorene product being insoluble and not readily dispersible in the body organic liquid at ambient temperature and the body of organic liquid being selected from the group consisting of non-polar hydrocarbon solvents that are not reactive with fluorenone and mixtures thereof;
   B) reacting the mixture prepared in step A) in the presence of at least one acidic condensing agent at a temperature effective to promote a reaction between the fluorenone and phenol compound and maintaining the temperature for a sufficient time to achieve the desired level of reaction completion between the fluorene and phenol compound;
   C) cooling the resulting mixture to a temperature effective to promote the precipitation of the crude bisphenol fluorene product, which temperature is less than or equal to 25° C.; and
   D) recovering the crude bisphenol fluorene product from the reaction mixture, the product having less than 20 weight percent of the phenol compound.

2. The process according to claim 1, wherein the body of organic liquid is selected from the group consisting of benzene, toluene, xylene, cyclohexane, hexane, heptane, trichloroethylene, 1,2-dichloroethane, methylene chloride, symtetrachloroethane, nitromethane and mixtures thereof.

3. The process according to claim 1, wherein the effective temperature in step B) is from 40° to 60° C.

4. The process according to claim 1, wherein the resulting mixture of step C) prior to cooling comprises an amount of the body of organic liquid and an amount of the bisphenol fluorene product, and the amount of the bisphenol fluorene product is 0.7 to 1.5 times the weight of the amount of the body of organic liquid.

5. The process according to claim 1, wherein concentrated sulfuric acid is used as the acidic condensing agent.

6. The process according to claim 1, wherein a mixture of concentrated sulfuric acid and mercaptocarboxylic acids is used as the acidic condensing agent.

7. The process according to claim 1, wherein gaseous hydrogen chloride is used as the acidic condensing agent.

8. The process according to claim 1, wherein gaseous hydrogen chloride and a bivalent, trivalent or tetravalent metal halide is used as the acidic condensing agent.

9. The process according to claim 1, wherein the acidic condensing agent is selected from the group consisting of organic sulfonic acids and mixtures thereof.

10. The process according to claim 9 wherein methanesulfonic acid is used as the acidic condensing agent.

11. The process according to claim 9, wherein a mixture of methanesulfonic and mercaptocarboxylic acids is used as the acidic condensing agent.

12. The process according to claim 9, wherein the phenol compound is employed in the reaction in a substantially stoichiometric amount.

13. The process according to claim 12, wherein the amount of the phenol compound employed in the reaction is less than 1.2 times the stoichiometric amount.

14. The process according to claim 13, wherein the amount of the phenol compound employed in the reaction is less than b 1.1 times the stoichiometric amount.

15. The process according to claim 9, wherein the mixture prepared in step (A) further comprises an organic thiol compound.

16. The process according to claim 15, wherein the organic thiol compound is selected from the group consisting of ethyl mercaptan, n-butyl mercaptan, 1-octyl mercaptan, t-dodecyl mercaptan, mercaptoethanol, mercaptoacetic acid and beta-mercapto propionic acid.

17. The process according to claim 1, wherein the bisphenol fluorene product is 9,9-bis-(4-hydroxyphenyl)-fluorene.

18. A crude bisphenol fluorene product having less than 20 weight percent of a phenol compound after recovery from a reaction mixture initially comprising fluorenone and the phenol compound.

19. A crude bisphenol fluorene product having less than 1 weight percent of a phenol compound after recovery from a reaction mixture initially comprising fluorenone and the phenol compound.

* * * * *

UNITED STATES PATENT AND TRADEMARK OFFICE
CERTIFICATE OF CORRECTION

PATENT NO. : 5,248,838

DATED : September 28, 1993

INVENTOR(S) : Sergio Massirio, Mauro Besio, Marcello Gagliano, Brunella Fornasari, Angelo Vallarino and Piero Di Mito It is certified that error appears in the above-indentified patent and that said Letters Patent is hereby corrected as shown below:

Col. 3, line 63, insert -- more -- after "or".

Col. 6, line 31, "is" should read -- it --.

Col. 6, line 58, "that" should read -- than --.

Col. 8, line 31, "methanesulionic" should read -- methanesulfonic --.

Col. 9, line 32, insert -- of -- after "body".

Col. 10, line 37, delete "b" after "than".

Signed and Sealed this

Eighteenth Day of April, 1995

BRUCE LEHMAN

*Commissioner of Patents and Trademarks*

*Attest:*

*Attesting Officer*